US008591924B2

(12) United States Patent
Zheng

(10) Patent No.: US 8,591,924 B2
(45) Date of Patent: Nov. 26, 2013

(54) HIGH-COVERAGE AND NATURAL-LOOKING COSMETIC COMPOSITIONS AND USES THEREOF

(75) Inventor: Tao Zheng, Nanuet, NY (US)

(73) Assignee: Avon Products, Inc., New York, NY (US)

( * ) Notice: Subject to any disclaimer, the term of this patent is extended or adjusted under 35 U.S.C. 154(b) by 272 days.

(21) Appl. No.: 12/565,000

(22) Filed: Sep. 23, 2009

(65) Prior Publication Data

US 2011/0070273 A1  Mar. 24, 2011

(51) Int. Cl.
*A61K 8/02* (2006.01)
*A61Q 1/08* (2006.01)
*A61Q 1/04* (2006.01)
*A61Q 1/10* (2006.01)

(52) U.S. Cl.
USPC ............... 424/401; 424/63; 424/64; 424/70.7

(58) Field of Classification Search
USPC ..................... 424/401, 63, 64, 70.7
See application file for complete search history.

(56) References Cited

U.S. PATENT DOCUMENTS

| 5,324,506 | A | * | 6/1994 | Calvo et al. ..................... 424/63 |
| 5,522,923 | A | * | 6/1996 | Kimura et al. ................ 106/418 |
| 5,599,547 | A | * | 2/1997 | Bartholomey et al. ....... 424/401 |
| 6,019,831 | A | * | 2/2000 | Schmidt et al. ............... 106/417 |
| 6,113,928 | A | * | 9/2000 | Nogueira et al. ............. 424/401 |
| 2004/0120908 | A1 | * | 6/2004 | Cohen et al. ..................... 424/63 |
| 2006/0013838 | A1 | | 1/2006 | Peng et al. |
| 2008/0038360 | A1 | * | 2/2008 | Zukowski et al. ............ 424/490 |
| 2008/0044366 | A1 | | 2/2008 | Dumousseaux |
| 2009/0155586 | A1 | | 6/2009 | Maitra et al. |

FOREIGN PATENT DOCUMENTS

WO    WO 2009/077356    *    6/2009

OTHER PUBLICATIONS

Elmastas, et al. Radical Scavenging Activity and Antioxidant Capacity of Bay Leaf Extracts. Journal of the Iranian Chemical Society, vol. 3, No. 3, Sep. 2006, pp. 258-266.*

* cited by examiner

*Primary Examiner* — Anoop Singh
*Assistant Examiner* — Anna Falkowitz
(74) *Attorney, Agent, or Firm* — David M. Joyal; Joan M. McGillycuddy; Brian C. Remy

(57) ABSTRACT

Topical compositions comprising at least one matte-finished interference pigment combined with one or more microsphere(s) and elastomer(s) are provided, as well as methods for using such compositions in cosmetics and dermatological products that afford high coverage of flaws or imperfections, while maintaining a natural-looking appearance. These cosmetics and dermatological products can improve the aesthetic appearance of skin, hair, or nails when topically applied thereto.

13 Claims, No Drawings

HIGH-COVERAGE AND NATURAL-LOOKING COSMETIC COMPOSITIONS AND USES THEREOF

FIELD OF INVENTION

The present invention relates generally to compositions for topical application which comprise matte-finished interference pigments combined with microspheres and elastomers, and the use of such compositions in cosmetics providing high-coverage but a natural-looking appearance.

BACKGROUND OF THE INVENTION

While consumers seek cosmetics that provide both coverage and a natural-look, there remains a continuing need in the cosmetic industry for such products. With color cosmetics, there is traditionally a trade-off between naturalness and coverage, where the better a cosmetic hides imperfections, the less natural it generally looks upon application. For example, non-pigmented products containing elastomers and microspheres often provide a natural look, but offer very little coverage. On the other hand, conventional colored foundations provide high-coverage, but less naturalness. While the desired coverage and color can come from the use of high-refractive index materials, such as titanium dioxide or other iron oxide pigments, such components are largely opaque and thus often appear monochromic, artificial, or paste-like, at least in part because they cover up natural color variations of human skin.

Natural skin has a transparent quality with color that varies depending upon the angle from which it is viewed, a phenomenon known as "color travel." The outer layer of human skin is a semi-transparent layer known as the stratum corneum. Underlying the stratum corneum is a layer of skin that has the blood vessels and pigments of the body. The reddish hue of the blood vessels, hemoglobin, and the brown/black hue of melanin combine to produce, through the transparency of the stratum corneum, the skin's color. Moreover, the angle of viewing of the skin alters its appearance to the viewer. For example, the viewer sees more of the red of hemoglobin in the skin's dermis when the skin is viewed at virtually a perpendicular angle. However, the viewer sees more brown, due to the melanin content of the outer layers of epidermis, when the skin is viewed at an acute angle. Color cosmetic manufacturers recognize that matching this color variation, while concealing textual and color imperfections, is important in providing a desirable cosmetic product, especially in foundation make-up products.

One earlier attempt to address these problems used large particle color travel pigments to supposedly retain the color travel effect upon application of powdered pigments to the skin. See, e.g., U.S. Pat. Appl. Pub. No. 2006/0013838. The pigments were coated with at least two layers of high and low refractive index metal oxides. Another approach involved the use of pigment particles having an inorganic core at least partially coated with an organic coloring substance. See, e.g., U.S. Pat. Appl. Pub. No. 2008/0044366. These methods involved complicated manufacturing procedures, e.g., with respect to the required layering or coating of specific materials in a specific manner. Still another approach used macroscopic particles coated with inorganic particles, while using little or no pigment (see U.S. Pat. Appl. Pub. No. 2009/0155586 to Avon Products, Inc.). This approach may result in low coverage cosmetics.

Accordingly, there remains a need in the cosmetic arts for colored cosmetic compositions affording high-coverage, e.g., that obscures both textural and color imperfections, while still maintaining the natural look of clean, bare skin. It is therefore an object of the invention to provide compositions and methods addressing these and other needs.

The foregoing discussion is presented solely to provide a better understanding of the nature of the problems confronting the art and should not be construed in any way as an admission as to prior art nor should the citation of any reference herein be construed as an admission that such reference constitutes "prior art" to the instant application.

SUMMARY OF THE INVENTION

In accordance with the foregoing objectives and others, it has surprisingly been found that compositions comprising matte-finished interference pigments, in combination with microspheres and elastomers, provide both high-coverage and natural-looking color, and thus find use as desirable cosmetic or dermatological products.

One aspect of the instant invention relates to cosmetic or dermatological compositions, comprising at least one matte-finished interference pigment combined with at least one microsphere and at least one elastomer, in a cosmetically acceptable vehicle. The matte-finished interference pigment, microsphere, and elastomer are present in amounts effective to afford high-coverage yet naturalness when the composition is topically applied to a biological surface. For example, in preferred embodiments, the cosmetic composition is capable of providing simultaneously higher coverage and naturalness than an otherwise identical cosmetic composition lacking at least one of the matte-finished interference pigment, microsphere, and elastomer.

In some preferred embodiments, the matte-finished interference pigment has a particle size of 10 to 60 μm, more preferably less than 40 μm, and comprises mica coated with titanium dioxide and further layered with at least one other metal. In some more preferred embodiments, the matte-finished interference pigment is of a red shade; the microsphere has a mean diameter of from 1 to 100 μm; and/or the elastomer comprises a blend dimethicone, cetearyl dimethicone crosspolymer, PEG/PPG-20/23 dimethicone, and BHT-BL. In some embodiments, the microsphere is at selected from the group consisting of cellulose, talc, zinc stearate, mica, kaolin, nylon powder, polyethylene powder, Teflon, starch, boron nitride, and silica. In some embodiments, the elasotmer is at least one hydrocarbon-based elastomer selected from the group consisting of styrene-butadiene-styrene block copolymer, nitrile rubber, SBR rubber, EPDM rubber, polyurethane elastomer, and polyester elastomer; and/or at least one silicon-based elastomer selected from the group consisting of dimethicone/vinyl dimethicone crosspolymer; dimethicone/phenyl vinyl dimethicone crosspolymer; and lauryl dimethicone/vinyl dimethicone crosspolymer.

In some embodiments, the matte-finished interference pigment; microsphere, and elastomer are in a ratio of 1-25:1-25:1-25, preferably 1:1:1 by weight. In some embodiments, each of the matte-finished interference pigment, microsphere, and elastomer is present in an amount from about 0.1 weight % to about 20 weight %, from about 0.5 weight % to about 15 weight %, from about 1 weight % to about 10 weight %, or from about 2 weight % to about 8 weight %, based on the total weight of the cosmetic composition. In more preferred embodiments the components will be in amounts effective to provide (i) at least 80 dry-film coverage; (ii) viewable color travel; and (iii) at least 20% higher chroma compared to the product lacking the MIP, microsphere, and/or elastomer, when the composition is topically applied to a biological surface, such as the skin, hair, or nails.

Another aspect of the instant invention relates to methods for making or using compositions comprising at least one matte-finished interference pigment combined with at least one microsphere and at least one elastomer. In some embodiments, a method for improving both coverage and naturalness of a cosmetic composition is provided, comprising: adding to the cosmetic composition an effective amount of each of a matte-finished interference pigment, a microsphere, and an elastomer to impart two or more of the following characteristics to the cosmetic composition: (i) at least 80 dry-film coverage; (ii) viewable color travel; and (iii) at least 20% higher chroma compared to the cosmetic composition without the inventive combination; thereby providing an improved cosmetic composition. In some embodiments, the cosmetic composition is formulated as a colored, high-coverage and natural-looking foundation, lip product or mascara.

For example, in a particularly preferred embodiment, a foundation composition is provided that comprises a matte-finished interference pigment, the matte-finished interference pigment having a particle size of 10 to 60 μm and comprising mica coated with titanium dioxide and further layered with at least one other metal oxide; a microsphere having mean diameter of from 1 to 100 μm; and an elastomer comprising a blend of dimethicone, cetearyl dimethicone crosspolymer, PEG/PPG-20/23 dimethicone, and BHT-BL, in a cosmetically acceptable vehicle, the vehicle comprising a volatile and non-volatile silicone oil; where the matte-finished interference pigment, microsphere, and elastomer are in a ratio of 1:1:1 by weight; and where the composition when applied to the skin imparts viewable color travel to enhance the natural appearance of the foundation.

In another aspect, methods are provided for improving the aesthetic appearance of a biological surface, such as the skin, hair, and nails. In some embodiments, a method is provided for providing skin, hair, and/or nails with high-coverage but a natural-look, comprising: applying a composition of the instant invention to the skin, hair, and/or nails, and allowing the composition to form a film, whereby the film provides the skin, hair, and/or nails with high-coverage but a natural-look. In some embodiments, the composition is applied to the skin, such as facial skin. In some embodiments, the composition is applied to hair, such as an eyelash.

These and other aspects of the invention will be better understood by reference to the following detailed description of the invention, figures, and appended claims.

DETAILED DESCRIPTION

The present invention relates to cosmetic and dermatological formulations which surprisingly provide high-coverage and a natural-look. The compositions comprise at least one matte-finished interference pigment in combination with one or more elastomers and one or more microspheres, a combination that surprisingly provides a natural-look while allowing a high level of coverage. Such compositions find use in color cosmetics, in particular foundations, that can conceal skin imperfections, while maintaining the color variations of natural skin. The compositions also find use in dermatological compositions and cosmetic products for the hair and nails.

Compositions Providing High-Coverage and a Natural-Looking Appearance

In one aspect, the instant invention relates to a cosmetic or dermatological composition comprising at least one matte-finished interference pigment combined with at least one microsphere and at least one an elastomer. A "matte-finished interference pigment," as used herein, refers to a pigment made up of particles coated with metal oxides that do not appear shiny. Matte-finished interference pigments thus are distinguished from conventional interference pigments that appear shiny upon application, such as pearlescent pigments. Rather, matte-finished interference pigments for use in the instant invention are those associated with a low sheen. The term "matte-finished interference pigment" is used interchangeably herein with "MIP" and with "matte-finished interference effect pigment."

In certain preferred embodiments, the MIP is metal oxide-coated mica, even more preferably titanium-dioxide ($TiO_2$) coated mica, which itself can be further treated with other metal oxides. Metal oxides include, without limitation, iron oxide and/or tin oxide, as well as $ZrO_2$, $SnO_2$, $ZNO$, $BiOCl$, $Fe_2O_2$, $Fe_3O_4$, $Cr_2O_3$, $CeO_3$, molybdenum oxides, $CoO$, $CO_3O_4$, $VO_2$, $V_2O_3$, $NiO$, $V_2O_5$, $CuO$, $Cu_2O$, $Ag_2O$, $CeO_2$, $MnO_2$, $Mn_2O_3$, $Mn_2O_5$, titanium oxynitrides, pseudobrookite, ilmenite, titanium nitride, $MoS_2$, $WS_2$, or mixtures or combinations thereof. The metal-oxide layers can be formed by any means known in the art and preferably are applied by wet-chemical methods, e.g., as described in U.S. Pat. Appl. Pub. No. 2006/0013838. Unlike the pigments in that case, however, the MIPs of the instant invention need not have alternating layers of high and low refractive index metal oxides. Nor do the MIPs need to have an inorganic core at least partially coated with an organic coloring substance, as described and required in U.S. Pat. Appl. Pub. No. 2008/0044366.

Examples of MIPs suitable for use in preferred embodiments of the instant invention include, but are not limited to, KTZ Interline and/or KTZ MultiColor from Taizhu Group, which use mica, titanium dioxide, and iron oxide; Ronaflair Balance/Red/Gold/Blue, Timiron Silk, Low Luster Pigment, and/or Extender W from EMD Chemicals; and any combinations thereof. Ronaflair Balance/Red/Gold/Blue are low luster interference fillers, manufactured bye EMD Chemicals, intended for use at about 3% to about 5% in, e.g., face powders and powder and liquid foundations. A single MIP type, or combinations or blends of two or more of the MIPs, may be used. For example, the amount and kind of MIPs can be varied for use on different skin color types.

In some preferred embodiments, the MIP has small particle size. By "small particle size" is meant that the particles have a median particle size (D50) of less than about 100 μm, preferably less than about 80 μm, more preferably less than about 60 μm, and even more preferably less than about 40 μm. In some embodiments, the MIP median particle size is in the range of about 10 to about 60 μm, with preference from about 20 to about 40 μm, or about 10 to about 30 μm. As used herein, "particle size" is used interchangeably with "median particle size," unless specifically indicated otherwise. Desired particle sizes of the MIPs can be obtained by conventional methods, e.g., by sieving or sedimentation.

In some preferred embodiments, the MIP is of a red shade. That is, the cosmetic composition comprises at least one red-shade MIP. It is believed that the red shade MIP mimics the colors of blood hemoglobin, visible through the stratum corneum, as discussed above, and thereby imparts naturally-multichromatic color to the skin.

In preferred embodiments, the MIP is a high-chroma MIP, such as a high-chroma red shade MIP having a particle size of about 20 to about 40 μm. Based on the teachings provided herein, one of skill in the art can recognize other matte-finished interference pigments that will find use in the compositions of the instant invention. For example, one of skill in the art can select an MIP having appropriate composition, particle size, and/or red shade suitable for one or more cosmetic applications described herein, e.g., to provide higher chroma MIPs. The higher chroma MIPs provide higher color intensity that is yet well-correlated with a natural look, and that can create an appearance of natural, healthy skin.

The selected MIP(s) is combined with one or more elastomers and one or more microspheres. "Microspheres" as used herein refers to any spherical, or substantially spherical, light-scattering particles having mean diameter in the micrometer range, e.g., from about 1 µm to about 1,000 µm (1 mm), preferably from about 0.1 to about 200 µm, more preferably from about 1 to about 100 µm. The spherical particles may be composed of various natural and/or synthetic materials and may be either solid and/or hollow. Preferred microspheres for use in the instant invention include, without limitation, cellulose, talc, zinc stearate, mica, kaolin, nylon powder, polyethylene powder, Teflon, starch, boron nitride, copolymer microspheres, such as Expancel, silica, silicone resin microbeads, such as Tospearl, commercially available from Momentive, and the like, as well as any combination thereof. Conventionally, microspheres are used as fillers, where their spherical shape provides a smooth feel upon application to the skin, in what has been described as "smooth ball bearing" texture. In certain preferred embodiments of the instant invention, the microspheres further provide coverage as well as producing a "soft-focus" effect to enhance the appearance of a natural look.

Elastomers can further enhance this look. As used herein "elastomer" refers to an amorphous polymer having the property of elasticity, wherein the elastomer is capable of dispersing the microsphere and MIP components in a cosmetically acceptable vehicle. The elastomers may be particulate or film-formers, but are preferably particulate and are preferably non-film-forming. The elastomer may be a hydrocarbon-based elastomer and/or a silicone-based elastomer. Illustrative, non-limiting examples of elastomers are natural and synthetic rubbers, for example, natural rubber, nitrile rubbers, hydrogenated nitrite rubbers, ethylene-propylene rubbers, polybutadiene, polyisobutylene, butyl rubber, halogenated butyl rubber, polymers of substituted butadienes, such as chlorobutadiene and isoprene, copolymers of vinyl acetate and ethylene terpolymers of ethylene, propylene, and a non-conjugated diene, and copolymers of butadiene with one or more polymerizable ethylenically unsaturated monomers such as styrene, acrylonitrile, and methyl methacrylate; silicone elastomers; fluoropolymers including fluoropolymers having a silicone backbone; polyacrylates; polyesters, polyacrylic esters, polyethers; polyamides, polyesteramides, polyurethanes, and mixtures thereof.

Silicone-based elastomers may comprise cross-linked silicone polymers derived from room temperature vulcanizable silicone sealant chemistry, or addition polymerized silicone elastomers prepared by the hydrosilylation of olefins or olefinic silicones with silyl hydrides. Skilled artisans understand how to obtain these silicone elastomers. Non-limiting examples of silicone elastomers include crosslinked organopolysiloxanes such as, for example, dimethicone/vinyl dimethicone crosspolymers, vinyl dimethicone/lauryl dimethicone crosspolymers, alkyl ceteayl dimethicone/polycyclohexane oxide crosspolymers, or mixtures thereof. Non-limiting examples of these elastomers include: cyclopentasiloxane (and) Dimethicone Crosspolymer: DC 9040 and DC 9045 commercially available from Dow Corning™ (Midland, Mich.), dimethicone/phenyl vinyl dimethicone crosspolymers, specifically, cross-linked methylpolysiloxanes under the tradenames KSG-15 (in decamethyl cyclopentasiloxane); KSG-16 (in low-viscosity methylpolysiloxane); and KSG-18 (in methylphenyl polysiloxane) commercially available from Shin Etsu Silicones of America, Inc. (Akron, Ohio); lauryl dimethicone/vinyl dimethicone crosspolymers supplied by Shin Etsu Silicones of America, Inc. (Akron, Ohio) (e.g., KSG-31 (lauryl dimethicone/copolyol crosspolymer), KSG32; vinyl dimethicone/lauryl dimethicone crosspolymers (KSG-41 in mineral oil; KSG-42 in isododecane; KSG-43 in triethylhexanoin; and KSG-44 in squalane), and the Gransil line of elastomers available from Grant Industries Inc. (Elmwood Park, N.J.) such as Dimethicone/Divinyldimethicone/Silsesquioxane Crosspolymer under tradename, EPSQ™. An embodiment of the invention utilizes a preferred silicone elastomer of EPSQ™.

Also suitable in some embodiments of the invention are silicone crosspolymers obtained by self polymerization of bifunctional precursor molecules containing both epoxy-silicone and silyl hydride functionalities to provide a silicone copolymer network in the absence of crosslinker molecules. Illustrative examples of such crosspolymers include the Velvesil™ line of silicone crosspolymers available from Momentive Performance Materials, Inc. (Wilton, Conn.; formerly GE Silicones); SFE 83™. (cyclomethicone (and) dimethicone/vinyldimethicone crosspolymer); and VELVESIL™ (cyclopentasiloxane (and) C30-45 alkyl dimethicone/polycyclohexene oxide crosspolymer), such as the VELVESIL™ 125.

Preferred examples of silicone-based elastomers for use in certain embodiments of the instant invention include dimethicone/vinyl dimethicone crosspolymers and lauryl dimethicone/vinyl dimethicone crosspolymers, and any combinations thereof. Dimethicone/vinyl dimethicone crosspolymers are commercially available from a variety of suppliers, such as Dow Corning (e.g., DC 9040 and DC 9041), Momentive (e.g., Velvesil 125 and derivatives), and Shin Etsu (e.g., KSG-15, 16, 18, which is a dimethicone/phenyl vinyl dimethicone crosspolymer). Lauryl dimethicone/vinyl dimethicone crosspolymers is also commercially available, e.g., from Shin Etsu (e.g., KSG-31, KSG-32, KSG-41, KSG-42, KSG-43, and KSG-44).

Preferred examples of hydrocarbon-based elastomers for use n certain embodiments of the instant invention include styrene-butadiene-styrene (SBS) block copolymer, nitrile rubber, SBR rubber, ethylene propylene-diene monomer (EPDM) rubber, as well as polyurethane elastomers, polyester elastomers, and the like, and any combination thereof. In some particularly preferred embodiments, the elastomer is a blend of dimethicone, cetearyl dimethicone crosspolymer, PEG/PPG-20/23 dimethicone, and BHT-BL, commercially available, e.g., from Momentive Performance Materials, 187 Danbury Rd, Wilton Conn. 06897, under the commercial name "Y-17483." PEG/PPG-20/23 dimethicone is the alkoxylated derivative of dimethicone comprising an average of 20 moles of ethylene oxide and 23 moles of propylene oxide. Additional non-volatile dimethicone is also used as the carrier.

The preferred particle size of the elasotmers ranges from about 1 to about 200 microns, more preferably from about 1 to about 50 microns. The elasomers can be prepared by conventional procedures, for example, by palletizing, cutting, or tearing a bale of the elastomeric material into shreds or small pieces, followed by chopping or grinding those shreds or small pieces into particles having the desired size. In addition, "wet" chemistry techniques known in the art may be used to form elasotmers of a particular size or distribution of particle sizes that are desirable.

In certain particularly preferred embodiments, the combination of MIP with microspheres and elastomers provides synergistic effects, to achieve high-coverage while maintaining a natural-looking appearance, when topically applied to a biological surface. Without wishing to be bound by theory, it is believed that the MIP and microsphere combination provides high-coverage; while the elastomer and microsphere combination provides the "soft-focus" effect, that enhances the appearance of a natural look, as described above. The microspheres and elastomers further act synergistically to fill in wrinkles and/or fine lines on the skin surface, producing a younger, rejuvenated, fresher look. Synergy is particularly apparent with respect to aesthetics of cosmetic compositions of the instant invention, in some preferred foundation embodiments. Example 1 below, for example, shows the results of panel testing compositions of the instant invention, where the inventive combination provided synergistic improvement in both coverage and naturalness ratings.

Another aspect of the invention relates to methods for making cosmetic and/or dermatological compositions described herein. The MIP-microsphere-elastomer combination of the instant invention can be prepared in any conventional manner, preferably by mixing and blending the components in any order. In some embodiments, the elatomer first is mixed with the microspheres, and the elastomer-microsphere mixture is then combined with the MIP. In some embodiments, the microsphere and MIP are blended together first, and then the elatomer is added. In some preferred embodiments, the components are directly mixed into other cosmetic formulations, e.g., to impart characteristics of high-coverage and color, while maintaining a natural-look upon application to a biological surface. Unlike earlier approaches, e.g., as described in U.S. Pat. Appl. Pub. No. 2009/0155586, the inventive compositions described herein do not need embedding. That is, MIP does not need to be embedded or coated onto the elatomers used, simplifying manufacture of the instant inventive compositions. Thus, in some embodiments, the MIP component is not so embedded and/or is not coated onto the elastomer component. Rather, the three components may simply be mixed and/or blended into existing conventional Cosmetic and/or dermatological formulations to improve coverage while maintaining naturalness.

Accordingly, another aspect of the invention relates to methods for improving both coverage and naturalness of cosmetic compositions. The MIP, microsphere, and elastomer components may be added altogether at once, or one or two of the components may be added at a time, in any order. In some preferred embodiments, the elastomer is first blended into the cosmetic formulation, followed by the microsphere, and finally the MIP. In some other preferred embodiments, the microsphere and MIP are blended together first and then added to the cosmetic formulation, followed by adding the elatomer. The MIP, microsphere, and elastomer components will be combined in appropriate ratios and in appropriate compositional percentages to afford a product with improved coverage and naturalness.

Compositions affording simultaneously higher coverage and naturalness will comprise MIP(s), microsphere(s), and elastomer(s), each in an amount effective. By "effective amount" or "amount effective" is meant an amount sufficient to impart one or more of the following characteristics to the product: (i) at least 80 dry-film coverage; (ii) viewable color travel; and (iii) at least 20% higher chroma compared to an otherwise identical product lacking the MIP, microsphere, and/or elastomer, when the composition is topically applied to a biological surface, such as the skin, hair, and/or nails.

"Chroma" as used herein refers to the colorfulness of a stimulus relative to the brightness of a stimulus that appears white under similar viewing conditions, and is a measure of the amount of color a material imparts to a surface when applied thereto. High chroma materials will generally impart noticeable, apparent, and even dramatic color to the surface to which they are applied. Addition of the MIP-microsphere-elastomer combination described herein can increase chroma of a material, when viewed from one or more angles, while maintaining high, preferably viewable, color travel. For example, in some preferred embodiments, chroma is increased by at least about 10%, at least about 20%, at least about 50%, at or least about 80%, from one or more angles, compared to that of the material without the MIP-microsphere-elastomer combination, or without at least one of the three components of the combination, when viewed from the same angle(s).

"Color travel" refers to the phenomenon where the color of a material on a surface appears to vary with the angle from which the surface is viewed. "Viewable color travel" refers to the situation where the angular dependent color change is noticeable to the naked human eye, such that a visually perceptible color travel effect on chroma with angular dependence is observed. As discussed above, this phenomenon of color visibly changing with angular dependence is observed in natural skin, and thus mimicking it provides a more natural-looking finish. The cosmetics industry has undertaken detailed studies of the optics of light absorption, reflection, and scattering in the skin to attempt to design a product that, when applied to the skin, will convey to the viewer the impression of a natural but flawless clean skin. See, for example, Nishikata et al., Cosmetics and Toiletries 112:39-55, 1997. Nonetheless, conventional high-coverage formulations have low color travel, meaning that the color appears uniform on a surface regardless of the angle from which the surface is viewed. In certain preferred embodiments, the compositions of the instant invention have high color travel, preferably viewable color travel, and more preferably color travel that matches the color travel of natural skin.

Chroma and color travel can be measured by various methods known in the art and/or described herein. For example, a color spectrometer can be used to measure chroma and Hunter L/A/B color scales at different angles (such as, e.g., 15°, 25°, 45°, 75°, and 110°), and the extent to which the A and B color scale readings vary with the view angle also determines color travel.

As well as having viewable color travel, the naturalness of a product is also correlated with high diffuse transmittance. High diffuse transmittance refers to the "soft-focus" effect that enhances a natural look. Diffuse transmittance can be measured by various methods known in the art and/or described herein. Example 2 below, for example, illustrates diffuse transmission of various combinations, where the inventive combination provided synergistic improvement in diffuse transmittance and hence naturalness.

"Dry-film coverage" refers to the extent a material can conceal imperfections in a surface to which it is applied and then allowed to dry to form a film thereupon. The extent of concealment can also be measured in terms of the "hiding power" or "covering power" of the material. Dry-film coverage can be tested by various methods known in the art and/or described herein. A standard test for measuring the hiding power of materials that dry to form a film, for example, is the Dry-Film Coverage Test Method based on ASTM D 6441-05. See Int. Pat. App. Pub. WO 2007/141169; and ASTM International Designation: D 6441-05 "Standard Test Methods for Measuring the Hiding Power of Powder Coatings," downloaded March 2008, and herein incorporated in its entirety by reference. The following formula can be used to measure coverage: Contrast ratio (Coverage) $(Cw)=100*Ro/Rw$;

where Rw refers to reflectance of the applied test film over a white substrate; Ro refers to reflectance of the applied test film over a black substrate, and where the luminous reflectance factor is measured by a Konica Minolta handheld spectrophotometer. The method involves drawing down a sample on a polyester film and a control mil thickness; waiting for 15 minutes for samples to dry; putting the polyester upon a LENETA card and measuring reflectance (L* value), Ro (black background) and Rw (white background) using the spectrophotometer. Each LENETA card can read 3 data points on the black background and this can be repeated for 6 different LENEAT cards. The 18 data points can be collected and the contrast ratio determined. For example, contrast ratio can be based on an average of these data points. The coverage values then can be normalized based on % solids in the formula to account for differences in film thickness. A high contrast ratio translates into a film with high coverage. Certain preferred embodiments of the instant invention provide dry-film coverage of at least about 50, at least about 80, at least about 100, at least about 150, or at least abut 200.

High-coverage is also correlated with high reflectance. Reflectance refers to the fraction of incident light that is reflected at an interface, so that a high-coverage composition is expected to have high reflectance. Reflectance can be measured by various methods known in the art and/or described herein. Example 2 below, for example, illustrates reflectance of various combinations, where the inventive combination provided synergistic improvement in reflectance, and hence coverage. Example 2 further illustrates the synergy achieved in combining the MIP, microsphere, and elastomer components, to produce compositions having both high reflectance and high diffuse transmittance, and thus both and high-coverage and naturalness.

In preferred embodiments, the MIP, microsphere, and elastomer components are present in the cosmetic or dermatological composition in effective proportions relative to one another. Effective proportion refers to the effective amount of a given component relative to the amounts of one or more other component(s) in combination with it in the cosmetic or dermatological composition. The terms "effective amount" and "amount effective", discussed above, include the concept of "effective proportion." In some particularly preferred embodiments, the three components, the MIP(s), microsphere(s), and elastomer(s), are each present in an amount from about 0.1 weight % to about 20 weight %, from about 0.5 weight % to about 15 weight %, from about 1 weight % to about 10 weight %, from about 2 weight % to about 8 weight %, or about 3 weight %, based on the total weight of the cosmetic composition. In even more preferred embodiments, the MIA, microsphere, and elastomer are in a ratio of about 1-100:1-100:1-100; about 1-50:1-50:1-50; about 1-25:1-25:1-25; about 1-10:1-10:1-10; about 1-5:1-5:1-5; about 1-2:1-2:1-2, or most preferably about 1:1:1 by weight.

Determination of an effective amount and/or effective proportion is within the capabilities of those skilled in the art, based on the teachings provided herein. For example, the amounts disclosed herein, particularly amounts provided in compositional embodiments, provide representative examples. A person of ordinary skill using techniques known in the art also can determine other effective amounts and/or effective proportions of the three components used together to impart high-coverage and color while maintaining naturalness. The amounts disclosed, along with the teachings presented herein, provide guidance to enable one of ordinary skill in the art to select those and other effective amounts and/or proportions of the corresponding components.

The compositions of the instant invention find use in cosmetic and dermatological formulations for topical application to a biological surface, and can provide a natural look while concealing surface imperfections, as described in more detail below.

Formulations Providing High-Coverage and Natural-Looking Color

The compositions according to the instant invention can be formulated in a variety of forms for application in the cosmetic and dermatological fields, in particular for topical application to a surface. For example, the compositions may be formulated in a variety of product forms suitable for application to the skin, nails, hair, eyelashes, or eyebrows. Forms of topical compositions include, for example, a powder, lotion, cream, liquid, anhydrous or aqueous base, serum, spray, aerosol, cake, ointment, essence, gel, paste, serum, toner, patch, pencil, pomade, solution, towelette, mask, mousse, stick, foam, elixir, concentrate, emulsion, balm, foam, or any other known in the cosmetic or dermatological arts.

In some preferred embodiments, the cosmetic compositions are formulated into different product forms for topical application to the skin, in particular where it is desired to conceal color and/or texture imperfections of the skin with a natural-looking, even color. For example, a consumer may desire high-coverage yet naturalness from a foundation, a lip product, an eye product, or other topical composition. A "topical composition" as used herein refers to a composition for use on an outer surface of the body, e.g., on the skin, e.g., on the skin of the face, lips, neck, hands, arms, stomach, back, legs, and the like; or for coating the surface of a keratin fiber, such as the hair, eyelashes, eyebrows, and the like. Mascara products, for example, are particularly intended for essentially longilinear keratin fibers, such as the eyelashes, eyebrows, and hair. In certain particularly preferred embodiments, the inventive compositions are formulated as colored, high-coverage, natural-looking foundations, lip products, or mascaras. For example, the inventive compositions can be formulated as foundations that provide coverage of blemishes and/or discolorations but leave the skin with a healthy, natural-look, thus enhancing the natural appearance of the foundation. Foundations include, but are not limited to, liquid, cream, mousse, pancake, compact, powder, stick, or like products created or reintroduced by cosmetic companies to even out the overall appearance and/or coloring of the skin, while appearing fresh and natural.

Other particular product forms for use with the inventive compositions include, without limitation, pressed powders, concealers, eye shadows, eye highlighter, eye liner, blusher, body powder, body lotion, body spray, bronzing powder, bronzing stick, body paints, brow colors, and the like. A consumer also may desire high-coverage yet naturalness from a hair product, e.g., a shampoo, conditioner, leave-in conditioner, mousse, or other topical compositions for the hair. It is contemplated that the use of compositions of the instant invention in hair products can provide natural-looking, healthy sheen to the hair, e.g., by coating hair strands with a low sheen colored formulation that yet maintains the natural variations in hair color. A consumer also may desire high-coverage yet naturalness from a nail product, e.g., a nail polish, nail base, or top coat.

Dermatological compositions will include, e.g., skin care products, such as those used to treat, protect, or care for the skin. Such products include, without limitation, moisturizers, cleansers, sunscreen, and the like, as well as anti-wrinkle or line-minimizing products, or treatments for reducing the appearance of dermatological problems that have harmed the aesthetic appearance of the skin. In some embodiments, the dermatological composition is applied directly to a skin flaw, e.g., to an acne lesion or scar, to reduce its visibility while maintaining the look of bare natural skin.

The cosmetic and/or dermatological formulation will comprise effective amounts of each of the MIP, microsphere, and elastomer components, and preferably in effective proportions relative to one another, to impart one or more of the following characteristics to the product: (i) at least 80 dry-film coverage; (ii) viewable color travel; and (iii) at least 20% higher chroma compared to an otherwise identical product lacking the MIP, microsphere, and/or elastomer, when the composition is topically applied to a biological surface, such as the skin, hair and/or nails. In some particularly preferred embodiments, the MIP(s), microsphere(s), and elastomer(s) are each present in an amount from about 0.1 weight % to about 20 weight %, from about 0.5 weight % to about 15 weight %, from about 1 weight % to about 10 weight %, from about 2 weight % to about 5 weight %, or about 3 weight %, based on the total weight of the cosmetic composition. In even more preferred embodiments, the MIP, microsphere, and elastomer are in a ratio of 1-25:1-25:1-25, and preferably 1:1:1, by weight.

The compositions of the present invention can include a cosmetically acceptable vehicle. As used herein, "cosmetically acceptable vehicle" can refer to conventional cosmetic or dermatological formulations to which the inventive combination of at least one MIP, elastomer, and microsphere can be added. Suitable vehicles include any vehicle for cosmetic, drug or medicament that is suitable for use in direct, safe contact with human tissues or human hair. Such vehicles may take the form of any known in the art suitable for application to skin, hair and/or nails, and may include, without limitation, hydrocarbons, glycerin, $C_{1-4}$ alcohols, fatty alcohols, fatty ethers, fatty esters, polyols, glycols, vegetable oils, mineral oils, liposomes, laminar lipid materials, silicone oils, and any combinations thereof.

The vehicle may comprise an aqueous phase, an oil phase, an alcohol phase, a silicone phase, individually or as mixtures thereof. The cosmetically acceptable vehicle may also comprise an emulsion. Non-limiting examples of suitable emulsions include water-in-oil emulsions, oil-in-water emulsions, silicone-in-water emulsions, water-in-silicone emulsions, wax-in-water emulsions, water-oil-Water triple emulsions or the like, for example, having the appearance of a cream, gel or micro-emulsions. The emulsion may include an emulsifier, such as a nonionic, anionic or amphoteric surfactant.

The aqueous phase of the emulsion may include water, as well as one or more additional solvents, including lower alcohols, such as ethanol, isopropanol, and the like. The volatile solvent may also be a cosmetically acceptable ester such as butyl acetate or ethyl acetate; ketones such as acetone or ethyl methyl ketone; or the like.

The oil phase of the emulsion preferably has one or more organic compounds, including emollients; humectants (such as butylene glycol, propylene glycol, Methyl gluceth-20, and glycerin); other water-dispersible or water-soluble components including thickeners such as veegum or hydroxyalkyl cellulose; gelling agents, such as high MW polyacrylic acid, i.e. CARBOPOL 934; and mixtures thereof. The emulsion may have one or more emulsifiers capable of emulsifying the various components present in the composition.

The oil phase may comprise one or more waxes, including for example, rice bran wax, carnauba wax, ouricurry wax, candelilla wax, montan waxes, sugar cane waxes, ozokerite, polyethylene waxes, Fischer-Tropsch waxes, beeswax, botanical waxes, microcrystalline wax, silicone waxes, fluorinated waxes, and any combination thereof. The oil phase may comprise one or more volatile and/or non-volatile silicone oils.

Based on the teachings herein, a person skilled in the art will be able to select any of these vehicles, or any other materials described herein, and/or an amount thereof, and/or a proportion thereof, such that high-coverage yet natural-look properties of the colored compositions of the instant invention can be conserved.

The composition may comprise one or more additional colorants. Suitable colorants, including pigments, lakes, and dyes, are well known in the art and are disclosed in the C.T.F.A. Cosmetic Ingredient Handbook, First Edition, 1988, the contents of which are hereby incorporated by reference. Organic pigments can include, for example, FD&C dyes, D&C dyes, including D&C Red, Nos. 2, 5, 6, 7, 10, 11, 12, 13, 30 and 34, D&C Yellow No. 5. Blue No. 1, Violet No. 2. Exemplary inorganic pigments include, but are not limited to, metal oxides and metal hydroxides such as magnesium oxide, magnesium hydroxide, calcium oxide, calcium hydroxides, aluminum oxide, aluminum hydroxide, iron oxides ($\alpha$-$Fe_2O_3$, $\beta$-$Fe_2O_3$, $Fe_3O_4$, FeO), red iron oxide, yellow iron oxide, black iron oxide, iron hydroxides, titanium dioxide, titanium lower oxides, zirconium oxides, chromium oxides, chromium hydroxides, manganese oxides, cobalt oxides, cerium oxides, nickel oxides and zinc oxides and composite oxides and composite hydroxides such as iron titanate, cobalt titanate and cobalt aluminate. Other suitable colorants include ultramarine blue (i.e., sodium aluminum silicate containing sulfur), Prussian blue, manganese violet, bismuth oxychloride, talc, mica, sericite, magnesium carbonate, calcium carbonate, magnesium silicate, aluminum magnesium silicate, silica, titanated mica, iron oxide titanated mica, bismuth oxychloride, and the like. Further, one or more chroma-methicone colorants may be used, e.g., chroma-lite yellow-methocone, chroma-lite red-methicone, and chroma-lite black-methicone.

The compositions may be formulated for application to the hair and may include temporary, semi-permanent, and permanent hair dyes. These may be oxidative hair dyes or direct hair dyes. Oxidative hair dyes typically comprise (i) an oxidizing agent, such as hydrogen peroxide, sodium perborate or persulfate, a bromate of sodium, calcium, or magnesium, sodium iodate, or the like, (ii) an alkalizing agent in an amount effective to obtain a pH in the range of about 9.5 to 10.5, and (iii) one or more dye intermediates which can react in the presence of the oxidizing agent to form a colored molecule. The dye forming intermediates include oxidative dye precursors (also known as a "base") and optionally color modifiers (or "couplers"). Suitable oxidative dye precursors include, without limitation, those disclosed in U.S. Pat. No. 7,449,029 to Nguyen, U.S. Pat. No. 7,458,995 to Daigo, U.S. Pat. No. 7,056,351 to Hammond et al., U.S. Pat. No. 6,740, 129 to Tsujino et al., U.S. Pat. No. 4,865,619 to Junino et al., the disclosures of which are hereby incorporated by reference herein. The oxidizing agent is preferably present from about 0.1% to about 6% by weight of the composition and the dye forming intermediates collectively will typically comprise from about 0.001% to about 5% by weight of the composition.

Direct dyes include, without limitation, nitro dyes, anthraquinone dyes and acid dyes, oil-soluble dyes, basic dyes, and dyes of vegetable origin. When present, direct dyes will typically comprise from about 0.0001% to about 5% by weight of the composition. Specific direct dyes contemplated to by useful include, without limitation, those disclosed in U.S. Pat. No. 7,449,029 to Nguyen, U.S. Pat. No. 7,056,346 to Maubru, U.S. Pat. No. 7,458,995 to Daigo, U.S. Pat. No. 6,746,492 to Kawai et al., the disclosure of which is hereby incorporated by reference.

When formulating the compositions as hair dye products, it may be desirable to add and amount of thickener, such as a cationic or anionic polymer, sufficient to prevent the dye from running when applied to the hair. Particular mention may be made are acrylic acid polymers and copolymers. The thickener will typically be present from about 0.01% to about 4% by weight of the composition.

Cosmetically acceptable vehicles for the cosmetic powder compositions may also include various fillers and/or additional components. Suitable fillers include without limitation silica, treated silica, talc, zinc stearate, mica, kaolin, Nylon powders such as Orgasol™, polyethylene powder, Teflon™, starch, boron nitride, copolymer microspheres such as Expancel™ (Nobel Industries), Polytrap™ (AMCOL Health & Beauty Solutions, Inc.) and silicone resin microbeads (Tospearl from Momentive Performance Materials), and the like.

Additional colorant/powder fillers include, but are not limited to, inorganic powders such as gums, chalk, Fuller's earth, kaolin, sericite, muscovite, phlogopite, synthetic mica, lepidolite, biotite, lithia mica, vermiculite, aluminum silicate, starch, alkyl and/or trialkyl aryl ammonium smectites, chemically modified magnesium aluminum silicate, organically modified montmorillonite clay, hydrated aluminum silicate, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powder such as polyamide resin powder (nylon powder), cyclodextrin, methyl polymethacrylate powder, copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as magnesium oxide; and stabilizers/rheology modifiers, for example, Bentone Gel and Rheopearl TT2. Other useful powders are disclosed in U.S. Pat. No. 5,688,831, and U.S. Pat. Appl. Pub. 2009/0142382, the disclosures of which are incorporated by reference.

The inventive compositions may optionally include preservatives. When present, the preservatives will include from about 0.01 to about 5% by weight, typically about 0.05 to about 4% by weight, and preferably about 0.1 to about 3% by weight % of the total composition.

In addition, the compositions contemplated by this invention can include one or more compatible cosmetically or dermatologically acceptable adjuvants commonly used and known by the skilled practitioner, such as fragrances, emollients, humectants, chelators, thickeners, perilla oil or perilla seed oil (such as those described in publication no. WO 01/66067, incorporated herewith) and the like, as well as other botanicals such as aloe, chamomile, and the like.

The compositions of the invention may optionally comprise other active and inactive ingredients typically associated with dermatological, cosmetic and personal care products, including, but not limited to, excipients, fillers, emulsifying agents, antioxidants, surfactants, additional film-formers, chelating agents, gelling agents, thickeners, emollients, humectants, moisturizers, vitamins, sodium ascorbyl/cholesteryl phosphate, minerals, viscosity and/or rheology modifiers, sunscreens, keratolytics, depigmenting agents, retinoids, hormonal compounds, alpha-hydroxy acids, trioxaundecanedioic acid, alpha-keto acids, anti-mycobacterial agents, antifungal agents, antimicrobials, antivirals, analgesics, lipidic compounds, anti-allergenic agents, H1 or H2 antihistamines, anti-inflammatory agents, anti-irritants, antineoplastics, immune system boosting agents, immune system suppressing agents, anti-acne agents, anesthetics, antiseptics, insect repellents, skin cooling compounds, skin protectants, skin penetration enhancers, exfollients, lubricants, fragrances, additional colorants, staining agents, depigmenting agents, hypopigmenting agents, preservatives, stabilizers, pharmaceutical agents, photostabilizing agents, optical diffusers, insect repellants, UV absorbers, UV blockers, antiperspirants, moisturizers, conditioners, and the like, and mixtures thereof. Based on the teachings herein, a person skilled in the art will be able to select any of these active or inactive ingredients, or any other materials described herein, and/or an amount thereof, and/or a proportion thereof, such that the desirable properties of the cosmetic or dermatological compositions of the instant invention can be conserved.

Examples of cosmetic formulations comprising at least one MIP, microsphere and elastomer, in accordance with the instant invention, are provided in the Examples below. For example, composition 5 of Example 1 provides an example of a foundation formulation comprising the MIP-microsphere-elastomer inventive combination.

Use of High-Coverage and Natural-Looking Compositions

Another aspect of the instant invention relates to cosmetic or dermatological use of compositions comprising at least one MIP in combination with one or more microspheres and one or more elastomers. Cosmetic or dermatological compositions comprising the MIP-microsphere-elastomer combination act synergistically to surprising afford high-coverage and high color, while maintaining a natural look of the skin, hair and/or nails, in particular, providing a more naturally flawless look when applied to the skin.

In some embodiments, methods for improving the appearance of a surface are provided. A cosmetic or dermatological composition described herein can be applied to a surface to form a film that improves appearance, in particular by providing high-coverage while maintaining a natural-look. The surface can be any biological or keratinous surface, such as the skin, hair, and/or nails, as discussed above. The inventive compositions can be applied to one or more areas of the skin, including, without limitation, the skin of the face, lips, forehead, neck, hands, arms, legs, chest, and/or back. In some embodiments, the inventive compositions are applied to the hair, such as of the hair of the head, eyelashes, eyebrows, beard, moustache, and the like. In some embodiments, the inventive compositions are applied to nail surfaces, such as, for example, the fingernails and toenails.

The inventive compositions may be applied onto a surface by using, e.g., the hands, fingers, cotton swabs, sponges, cosmetic brushes, applicators, or the like, e.g., to spread the composition onto the surface. The inventive compositions may be applied directly to the surface, e.g., directly onto a surface of bare skin, or may be applied over a first layer of another product, for example, as when applied over moisturizer on the skin.

Improvement in aesthetic appearance involves providing the surface with high-coverage yet a natural look, as described herein. High-coverage typically affords a reduction in the appearance, noticeability, or visibility of at least one flaw on the surface, where a flaw refers to any unwanted textural and/or color occurrence on the surface. "Flaw" herein is used interchangeably with "imperfection." Skin flaws or imperfections can include, without limitation, wrinkles, fine lines, scars, blemishes, acne, freckles, mottled spots, age spots, or any other imperfections resulting from chronological or photo-damage of the skin, or other causes. Aesthetic appearance is also improved by optical blurring of such flaws, while maintaining a natural look. Optical blurring describes the "soft-focus" effect of diffuse transmittance, where a flaw is blurred and thus appears lessened or less noticeable, upon application of the inventive composition. In preferred embodiments, the result is skin that looks fresher, younger, healthier, and/or naturally flawless.

The cosmetic or dermatological composition generally is applied and then allowed to form a thin film on the surface to be improved. In some embodiments, the film has a thickness of about 2 microns and 50 microns. Applications may be applied anywhere in need of aesthetic improvement where the composition remains on the skin, and is preferably not removed or rinsed off the skin until desired. In some embodiments, the cosmetic or dermatological composition may be applied daily, every other day, or whenever desired, e.g., depending on the intended use. The practitioner will appreciate the routine and technique for applying such compositions and as needed.

Based on the teachings provided herein, one of skill in the art will recognize other cosmetic or dermatological applications for the compositions described herein, and such applications are also contemplated as within the scope of the instant invention. For example, inventive compositions comprising at least one MIP, microsphere, and elastomer may also find use in personal care products, for example, where it is desirable to achieve high-coverage with a natural-looking color.

EXAMPLES

Example 1

Synergistic Coverage and Naturalness by Inventive Combinations

As indicated in Table 1 below, five formulations were prepared, and tested by a panel of five individuals. "Vehicle" (composition 1) refers to typical foundation formulation, to which the elastomer, microsphere, and/or MIP are added. Each panelist applied each of the five formulations to the hand to evaluate coverage and naturalness. The panelists rated each of the formulations for either coverage or naturalness, separately, on a scale of 1 to 5, with 1 being the worst and 5 the best rating, and the ratings then were averaged.

The silicone elastomer plus vehicle (composition 2) received ratings little different from the vehicle composition. The addition of microspheres instead of elastomer (composition 3) increased both the naturalness and coverage ratings somewhat. The addition of an MIP instead of the elastomer or microspheres (composition 4) increased coverage ratings. The combination of the MIP together with the elastomers and microspheres, however, produced synergistic results. Namely, composition 5 showed a synergistic improvement in both coverage and naturalness ratings.

TABLE 1

| Function | Ingredients | 1 | 2 | 3 | 4 | 5 |
|---|---|---|---|---|---|---|
| MIP Pigment | Ronaflair Balance/Red/Gold/Blue | | | | 9 | 3 |
| Microsphere | NYLON POWDER-EXTRA FINE | | | 5 | | 2 |
| Microsphere | CELLULOSE-BEADS | | | 4 | | 1 |
| Elastomer | Y-17483 | | 9 | | | 3 |
| Vehicle | Dow Corning 200 Fluid, 10,000 cst | 60 | 51 | 51 | 51 | 51 |
| Vehicle | SILICONE FLUID SF-96-5 5 cst | 15 | 15 | 15 | 15 | 15 |
| Vehicle | CYCLOMETHICONE-PENTAMER | 25 | 25 | 25 | 25 | 25 |
| Ratings | Averaged Coverage (C) | 1 | 1 | 2.8 | 3.6 | 3.4 |
| | Averaged Naturalness (N) | 1.8 | 2 | 2.4 | 2.2 | 3.2 |
| Synergy-reflecting Parameter | C × N/100 | 1.8 | 2.0 | 6.7 | 7.9 | 10.9 |

Moreover, Table 1 also shows a synergy-reflecting parameter, obtained by multiplying the values for averaged coverage (C) by that for averaged naturalness (N) and dividing by 100. The suitability of the MIP-microsphere-elastomer combination in improving both coverage and naturalness is reflected in the product of C and N, and hence this parameter is useful in evaluating the ability of the inventive combination to simultaneously achieve both functions. As illustrated in Table 1, composition 5 has the highest synergy-reflecting parameter, thus even more clearly demonstrating the synergistic improvement in both coverage and naturalness. These results suggest that compositions comprising the inventive combination of at least one MIP, microsphere, and elastomer can be used in cosmetic or dermatological compositions to improve aesthetic appearance, by providing high-coverage, while yet maintaining a natural-looking color, based on the ratings of five individual panelists.

Example 2

Synergistic Coverage and Naturalness by Inventive Combinations

As indicated in Table 2 below, six additional formulations were prepared, and tested for reflectance (correlated with high-coverage) and diffuse transmittance (correlated with naturalness). Measurements were made using a GretagMacbeth Color-Eye® 700A Reference Spectrophotometer.

The silicone elastomer alone (composition 6) showed low reflectance and low diffuse transmission. The addition of microspheres (composition 7) increased diffuse transmittance, creating a "soft-focus" effect and thus enhancing naturalness. The addition of an MIP instead of the elastomer (compositions 8 and 10) increased reflectance, and thus enhanced coverage. The combination of the MIP together with the elastomers and microspheres, however, produced synergistic results. Namely, compositions 9 and 11 showed a synergistic improvement in both reflectance and diffuse transmittance.

TABLE 2

| Function | Ingredients | 6 | 7 | 8 | 9 | 10 | 11 |
|---|---|---|---|---|---|---|---|
| Elastomer | Y-17483 | 100 | 95 | 95 | 90 | 95 | 90 |
| Microsphere | POLYETHYLENE 1-20 MICRONS | | 5 | | 5 | | 5 |
| MIP Pigment | KTZ Interfine Red | | | 5 | 5 | | |
| MIP Pigment | Ronaflair Balance/Red/Gold/Blue | | | | | 5 | 5 |
| Results | Reflectance 400-700 nm (R) | 14 | 13 | 19 | 18 | 17 | 19 |
| | Diffuse Transmittance 400-700 nm (D) | 57 | 71 | 54 | 62 | 56 | 62 |
| Synergy-reflecting Parameter | R × D/100 | 0.8 | 0.9 | 1.0 | 1.1 | 0.95 | 1.2 |

Moreover, Table 2 also shows a synergy-reflecting parameter, obtained by multiplying the values for reflectance (R) by that for diffuse transmittance (D) and dividing by 100. The suitability of the MIP-microsphere-elastomer combination in improving both coverage (correlated with high reflectance) and naturalness (correlated with high diffuse transmittance) is reflected in the product of R and D, and hence this parameter is useful in evaluating the ability of the inventive combination to simultaneously achieve both functions. As illustrated in Table 2, compositions 9 and 11 have the highest synergy-reflecting parameters, thus even more clearly demonstrating the synergistic improvement in both reflectance and diffuse transmittance. These results suggest that compositions comprising the inventive combination of at least one MIP, microsphere, and elastomer can be used in cosmetic or dermatological compositions to improve aesthetic appearance, by providing high-coverage (correlated with high reflectance) while yet maintaining a natural-looking color (correlated with high diffuse transmittance).

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

The invention claimed is:

1. A cosmetic composition comprising:
   a red shade matte-finished non-pearlescent interference pigment, said red shade matte-finished non-pearlescent interference pigment having a particle size of from 10 to 60 μm and comprising mica coated with titanium dioxide and further layered with at least one other metal oxide;
   a microsphere; and
   an elastomer,
   in a cosmetically acceptable vehicle,
wherein said cosmetic composition imparts viewable color travel and provides simultaneously higher coverage and naturalness when applied to skin compared to an otherwise identical cosmetic composition lacking at least one of said red shade matte-finished non-pearlescent interference pigment, said microsphere, and said elastomer.

2. The cosmetic composition according to claim 1, wherein said red shade matte-finished non-pearlescent interference pigment has a particle size less than 40 μm.

3. The cosmetic composition according to claim 1, wherein said microsphere is selected from the group consisting of cellulose, talc, zinc stearate, mica, kaolin, nylon powder, polyethylene powder, Teflon, starch, boron nitride, and silica.

4. The cosmetic composition according to claim 1, wherein said elastomer is at least one hydrocarbon-based elastomer selected from the group consisting of styrene-butadiene-styrene block copolymer, nitrile rubber, SBR rubber, EPDM rubber, polyurethane elastomer, and polyester elastomer.

5. The cosmetic composition according to claim 1, wherein said elastomer is at least one silicon-based elastomer selected from the group consisting of dimethicone/vinyl dimethicone crosspolymer; dimethicone/phenyl vinyl dimethicone crosspolymer; and lauryl dimethicone/vinyl dimethicone crosspolymer.

6. The cosmetic composition according to claim 1, wherein said elastomer comprises a blend of cetearyl dimethicone crosspolymer and PEG/PPG-20/23 dimethicone.

7. The cosmetic composition according to claim 1, wherein said red shade matte-finished non-pearlescent interference pigment, said microsphere, and said elastomer are in a ratio of 1-25:1-25:1-25 by weight.

8. The cosmetic composition according to claim 7, wherein said red shade matte-finished non-pearlescent interference pigment, said microsphere, and said elastomer are in a ratio of 1:1:1 by weight.

9. The cosmetic composition according to claim 8, wherein each of said red shade matte-finished non-pearlescent interference pigment, said microsphere, and said elastomer is present in an amount of 2 weight % to 8 weight % based on the total weight of the composition.

10. A colored, high-coverage and natural-looking foundation comprising the cosmetic composition according to claim 1.

11. A colored, high-coverage and natural-looking lip product comprising the cosmetic composition according to claim 1.

12. A colored, high-coverage and natural-looking mascara comprising the cosmetic composition according to claim 1.

13. A colored or colorless foundation composition comprising:
   a matte-finished non-pearlescent interference pigment, said matte-finished non-pearlescent interference pigment having a particle size of 10 to 60 μm and comprising mica coated with titanium dioxide and further layered with at least one other metal oxide;

a microsphere having mean diameter of from 1 to 100 µm; and an elastomer comprising a blend of cetearyl dimethicone crosspolymer and PEG/PPG-20/23 dimethicone, in a cosmetically acceptable vehicle, said vehicle comprising a volatile and non-volatile silicone oil;

wherein said matte-finished non-pearlescent interference pigment, said microsphere, and said elastomer are in a ratio of 1:1:1 by weight;

and wherein said foundation composition applied to skin imparts viewable color travel to enhance the natural appearance of said foundation and provides simultaneously higher coverage and naturalness when applied to skin compared to an otherwise identical foundation composition lacking at least one of said matte-finished non-pearlescent interference pigment, said microsphere, and said elastomer.

* * * * *